United States Patent
Urman et al.

(10) Patent No.: US 12,097,071 B2
(45) Date of Patent: Sep. 24, 2024

(54) LEFT ATRIAL APPENDAGE (LAA) TRANSSEPTAL ACCESS POINT OPTIMIZATION

(71) Applicant: BIOSENSE WEBSTER (ISRAEL) LTD., Yokneam (IL)

(72) Inventors: Roy Urman, Irvine, CA (US); Liron Shmuel Mizrahi, Kiryat Bialik (IL); Amit Agarwal, Huntington Beach, CA (US)

(73) Assignee: Biosense Webster (Israel) Ltd., Yokneam (IL)

(*) Notice: Subject to any disclaimer, the term of this patent is extended or adjusted under 35 U.S.C. 154(b) by 444 days.

(21) Appl. No.: 17/088,082

(22) Filed: Nov. 3, 2020

(65) Prior Publication Data

US 2022/0133261 A1    May 5, 2022

(51) Int. Cl.
| | |
|---|---|
| A61B 8/08 | (2006.01) |
| A61B 8/00 | (2006.01) |
| A61B 8/12 | (2006.01) |
| A61B 17/12 | (2006.01) |

(52) U.S. Cl.
CPC ............ *A61B 8/0883* (2013.01); *A61B 8/085* (2013.01); *A61B 8/12* (2013.01); *A61B 8/445* (2013.01); *A61B 8/483* (2013.01); *A61B 17/12122* (2013.01); *A61B 17/12136* (2013.01); *A61B 2017/1205* (2013.01)

(58) Field of Classification Search
None
See application file for complete search history.

(56) References Cited

U.S. PATENT DOCUMENTS

| | | | |
|---|---|---|---|
| 8,663,268 B2 | 3/2014 | Quinn et al. | |
| 10,076,335 B2 | 9/2018 | Zaver et al. | |
| 2006/0135961 A1 | 6/2006 | Rosenman et al. | |
| 2007/0149995 A1 | 6/2007 | Quinn et al. | |
| 2010/0286718 A1* | 11/2010 | Kassab | A61M 25/10 606/158 |
| 2011/0092811 A1* | 4/2011 | Yasui | A61M 5/52 382/128 |
| 2011/0276075 A1 | 11/2011 | Fung et al. | |

(Continued)

OTHER PUBLICATIONS

International Search Report mailed Jan. 26, 2022 from corresponding PCT Patent Application No. PCT/IB2021/059824.

(Continued)

*Primary Examiner* — Shahdeep Mohammed
(74) *Attorney, Agent, or Firm* — Troutman Pepper Hamilton Sanders LLP

(57) ABSTRACT

A method includes, using a processor, identifying a septum and a Left Atrium Appendage (LAA) of a heart of a patient in an anatomical map of at least part of the heart. An entry surface over which a medical device is defined on the anatomical map, which is to be delivered via a sheath that penetrates the septum, is to engage with the LAA. A normal to the entry surface is calculated. A plurality of curves is calculated that each (i) have one end that is tangent to the normal, (ii) have a second end touching the septum, and (iii) comply with specified mechanical properties of the sheath. Multiple candidate locations on the septum are derived from the curves, for transseptal puncture with the sheath. The multiple candidate locations are presented to a user.

14 Claims, 2 Drawing Sheets

(56) References Cited

U.S. PATENT DOCUMENTS

| | | |
|---|---|---|
| 2018/0125581 A1 | 5/2018 | Wang et al. |
| 2019/0000551 A1* | 1/2019 | Sone .................. A61B 8/466 |
| 2019/0008591 A1* | 1/2019 | Desai .................. G06T 7/0012 |
| 2019/0090951 A1 | 3/2019 | Camus et al. |
| 2019/0183577 A1 | 6/2019 | Fahim et al. |

OTHER PUBLICATIONS

Jayender, J. et al., "Optimal Transseptal Puncture Location for Robot-Assisted Left Atrial Catheter Ablation", International Journal of Medical Robotics and Computer Assisted Surgery, (online) vol. 7, No. 2, Jun. 1, 2011, pp. 193-201.
https://en.wikipedia.org/wiki/Left_atrial_appendage_occlusion.
International Preliminary Report on Patentability dated May 8, 2023, from corresponding PCT Patent Application No. PCT/IB2021/059824.

* cited by examiner

LEFT ATRIAL APPENDAGE (LAA) TRANSSEPTAL ACCESS POINT OPTIMIZATION

FIELD OF THE INVENTION

The present invention relates generally to treatment planning for a medical probe, and particularly to planning occlusion of a left atrium appendage (LAA) using transseptal access for an invasive medical device.

BACKGROUND OF THE INVENTION

Various methods for planning a left atrium appendage (LAA) treatment using a catheter were proposed in the patent literature. For example, U.S. Patent Application Publication 2019/0090951 describes an ultrasound imager that is provided for LAA closure guidance. Using ultrasound imaging allows for anatomical modeling over time (e.g., throughout a heart cycle). An anatomy model of the LAA over time is used to create a biomechanical model personalized to the patient. The personalized models and a model of one or more closure devices are used to select a closure device for the patient, appropriate for the entire heart cycle and to guide placement of the selected closure device during an implantation.

SUMMARY OF THE INVENTION

An embodiment of the present invention that is described hereinafter provides a method including, using a processor, identifying a septum and a Left Atrium Appendage (LAA) of a heart of a patient in an anatomical map of at least part of the heart. An entry surface over which a medical device is defined on the anatomical map, which is to be delivered via a sheath that penetrates the septum, is to engage with the LAA. A normal to the entry surface is calculated. A plurality of curves is calculated that each (i) have one end that is tangent to the normal, (ii) have a second end touching the septum, and (iii) comply with specified mechanical properties of the sheath. Multiple candidate locations on the septum are derived from the curves, for transseptal puncture with the sheath. The multiple candidate locations are presented to a user.

In some embodiments, the specified mechanical properties of the sheath include a minimal radius of curvature of the sheath obtainable inside the heart by external manipulation of the sheath.

In some embodiments, defining the entry surface includes (a) delineating an ostium of the LAA on the anatomical map, and (b) best fitting a plane to the delineated ostium.

In an embodiment, calculating the curves depends on whether an access position of the sheath to a right atrium (RA) of the heart is from the inferior vena cava or from the superior vena cava.

In an embodiment, the medical device is an LAA occlusion device. In another embodiment, the medical device is one of a balloon catheter and a basket catheter.

In some embodiments, uploading the anatomical map includes obtaining the anatomical map using an invasive ultrasound probe.

In some embodiments, presenting the multiple candidate locations includes presenting the sheath, the entry surface, the normal and the candidate locations on the septum, using a 3D mapping system.

There is additionally provided, in accordance with another embodiment of the present invention, a system including a memory and a processor. The memory is configured to store an anatomical map of at least part of a heart of a patient. The processor is configured to: (a) identify a septum and a Left Atrium Appendage (LAA) of the heart in the anatomical map, (b) define on the anatomical map an entry surface over which a medical device, which is to be delivered via a sheath that penetrates the septum, is to engage with the LAA, (c) calculate a normal to the entry surface, (d) calculate a plurality of curves that each (i) have one end that is tangent to the normal, (ii) have a second end touching the septum, and (iii) comply with specified mechanical properties of the sheath, (e) derive from the curves multiple candidate locations on the septum, for transseptal puncture with the sheath, and (f) present the multiple candidate locations to a user.

The present invention will be more fully understood from the following detailed description of the embodiments thereof, taken together with the drawings in which:

DETAILED DESCRIPTION OF EMBODIMENTS

Overview

Figure 1:
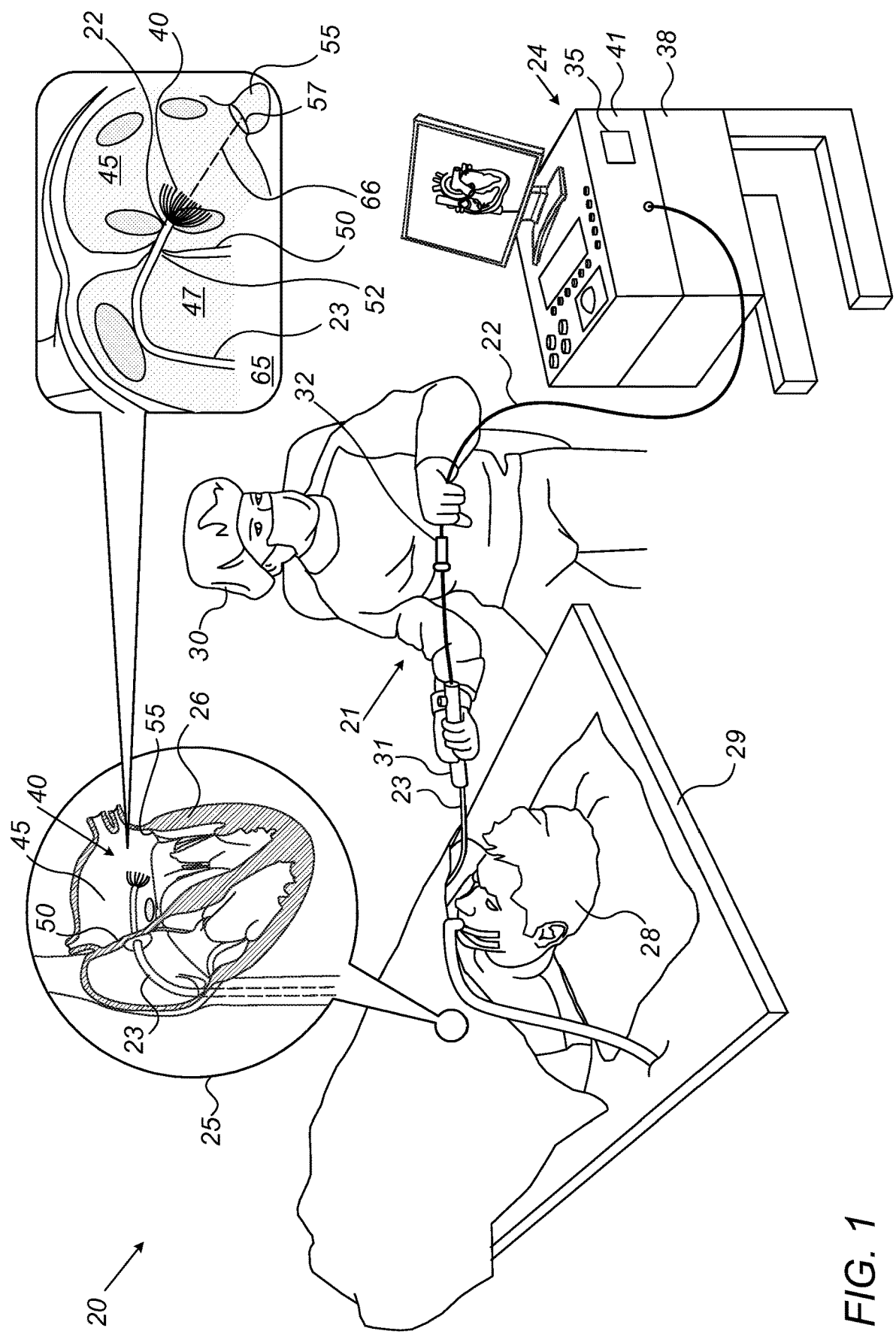
FIG. 1 is a schematic, pictorial illustration of a catheterization system comprising a catheter carrying a left atrial appendage (LAA) occlusion device, in accordance with an embodiment of the present invention.

Catheterization is an established therapy to control atrial fibrillation (AF) of a left atrium (LA). To access the LA with the catheter, a physician typically first introduces the catheter to the right atrium (RA) via the body vasculature, and pierces the septum dividing the left and right atria with a sheath of the catheter. The physician then threads the sheath into the LA through the pierced location and delivers via a sheath a medical device (e.g., a catheter) to engage with an LA tissue.

Proper selection of the transseptal piercing location is important, as it substantially impacts on obtaining stable contact with the septum wall tissue, advancing the sheath into a particular LA target location, and maintaining catheter position at the target LA location during the invasive treatment.

To complicate matters, the physician has to further carefully consider the transseptal piercing location, since its location may limit the ways an invasive device (e.g., a catheter) can be introduced to the RA. Specifically, a catheter can be introduced into the RA either via the inferior vena cava or the superior vena cava, and the choice of the two options may depend on the selected piercing location.

Moreover, the ability to subsequently control a catheter inside the LA depends on which remote vein is selected for the entry to the body, through which the sheath is navigated to either the inferior vena cava or superior vena cava of the RA. A combination of the above considerations, together with a given medical profile of the patient, may therefore limit a physician's options to perform a successful catherization process in the LA.

An invasive procedure that requires particularly careful consideration of the transseptal piercing location is occlusion of the left atrial appendage (LAA). Such a procedure is used to reduce the probability of blood clots forming in the appendage, which is likely to happen in certain patients with AF. The LAA is occluded by a catheter deploying an LAA occlusion device. The occlusion procedure requires careful angular alignment of the catheter relative to an ostium of the LAA in order to have a successful outcome. However, because of limitations on the flexibility and maneuverability of the sheath and the catheter, it is not simple to navigate a catheter to the LAA successfully from a suboptimal septum piercing location.

Embodiments of the present invention that are described hereinafter provide a technique to find multiple candidate septum locations and directions for septum penetration for invasive devices, such as a catheter carrying a LAA occlusion device, to accurately engage a given LA target, such as the LAA. Using the disclosed technique gives a physician the ability to consider multiple potential locations for septum penetration, leading to an increased choice of both clinically valid RA access approaches available to the physician and suitable invasive medical devices (e.g., LAA devices). Such a larger selection is important, considering, for example, a medical condition (e.g., RA enlargement) of a given patient which may, to begin with, limit a physician's catheterization options.

In some embodiments, a processor carries out the disclosed technique for finding one or more candidate septum-piercing locations to access the LAA, by performing the following steps:

Generating a 3D anatomical model (e.g., anatomical map) of the relevant region (e.g., a region encompassing the septum and the LAA).

Defining a landing site for the LAA device, i.e., an aperture of the LAA through which the catheter is inserted into the LAA, taking into account the type of occlusion device and the LAA shape. Such a landing site is defined, for example, by delineating an ostium of the LAA in a form of a closed curve over the 3D anatomical model.

Fitting an entry surface (e.g., a plane) that is substantially parallel to the delineated LAA ostium at the landing site, and calculating a normal to this plane.

Using predefined mechanical properties of the sheath used to deliver the device, calculating a plurality of curves that each (i) have one end that is tangent to the normal, (ii) have a second end touching the septum, and (iii) comply with specified mechanical properties of the sheath.

Deriving from the curves multiple candidate locations on the septum, for transseptal puncture with the sheath, thus creating, at one or more respective intersections of the curves with the septum, one or more respective potential access points for the transseptal puncture.

Presenting the multiple candidate locations to a user.

Examples of the mechanical properties include a minimal radius of curvature and a maximal deflection angle achievable with the sheath, and a location over the sheath at which a distal end of the sheath can be bent (to access the LAA).

In an embodiment, the processor overlays the identified septum locations on the anatomical map, so that the physician performing the LLA occlusion procedure could select, for example, a most suitable RA approach (e.g., inferior or superior) to the LAA with a given LAA occlusion device. The sheath, the landing site (e.g., entry surface), the normal and the transseptal puncture (also called "access") point are all visualized in a 3D mapping system (e.g., CARTO®).

Typically, the processor is programmed in software containing a particular algorithm that enables the processor to conduct each of the processor-related steps and functions outlined above.

By identifying one or more candidate septum locations that may be optimal to pierce to reach the LAA, the disclosed technique may increase the chances, for a variety of cardiac patients, of successful completion of an invasive procedure of the LAA.

System Description

FIG. 1 is a schematic, pictorial illustration of a catheterization system 20 comprising a catheter 21 carrying a left atrial appendage (LAA) occlusion device 40, in accordance with an embodiment of the present invention. A distal end of a shaft 22 of the catheter is inserted by a physician 30 through a sheath 23 into a left atrium 45 of heart 26, seen in inset 25, of a patient 28 lying on a table 29. During the insertion of shaft 22, LAA occlusion device 40 is maintained in a collapsed configuration by sheath 23. By containing LAA occlusion device 40 in a collapsed configuration, sheath 23 also serves to minimize vascular trauma along the way to the target location.

To reach left atrium appendage (LAA) 55 inside left atrium (LA) 45, seen in inset 65, physician 30 first navigates sheath 23 to the inferior vena cava access approach of a right atrium 47. The physician then pierces a hole 52 in a septum 50 dividing the atria with sheath 23 by manipulating, for example, a manipulator 32 near the proximal end of the catheter and/or deflection from sheath 23. When inside LAA 55, the physician advances, via sheath 23, a distal end of a shaft 22 and deploys LAA occlusion device 40, coupled to a distal edge of the shaft, inside LAA 55.

Physician 30 then maneuvers sheath 23 of catheter 21 inside LA 45 using catheter handle 31 so as to access and contact LAA 55. As further seen in inset 65, to successfully access LAA 55, the physician aligns the sheath 23 at a particular direction 66 that points to an ostium 57 of LAA 55.

The proximal end of catheter 21 is connected to a control console 24. In the embodiment described herein, catheter 21 may be used for any suitable therapeutic and/or diagnostic purpose, such as electrical sensing, or the aforementioned LAA occlusion in heart 26, among other possible medical usages of such catheters.

Control console 24 comprises a processor 41, typically a general-purpose computer, with a suitable front end and interface circuits 38 for receiving signals from catheter 21, as well as for applying treatment via catheter 21 in heart 26 and for controlling the other components of system 20. Processor 41 typically comprises a general-purpose computer which is programmed in software to carry out the functions described herein. The software may be downloaded to a memory 35 of the computer in electronic form, over a network, for example, or it may, alternatively or additionally, be provided and/or stored on non-transitory tangible media, such as magnetic, optical, or electronic memory. In particular, processor 41 runs a dedicated algorithm as disclosed herein, including in FIG. 3, that enables processor 41 to perform the disclosed steps, as further described below.

The example configuration shown in FIG. 1 is chosen purely for the sake of conceptual clarity. The disclosed techniques may similarly be applied using other system components and settings. For example, other devices, such as a balloon catheter or a basket catheter, may be used. An anatomical map can be generated by system 20 employing an invasive ultrasound (US) probe, such as by the CARTO-SOUND® Module with SOUNDSTAR® catheter. As another example, system 20 may comprise other components, such as for cardiac tissue temperature sensing.

Left Atrial Appendage (LAA) Transseptal Access Point Optimization

Figure 2:
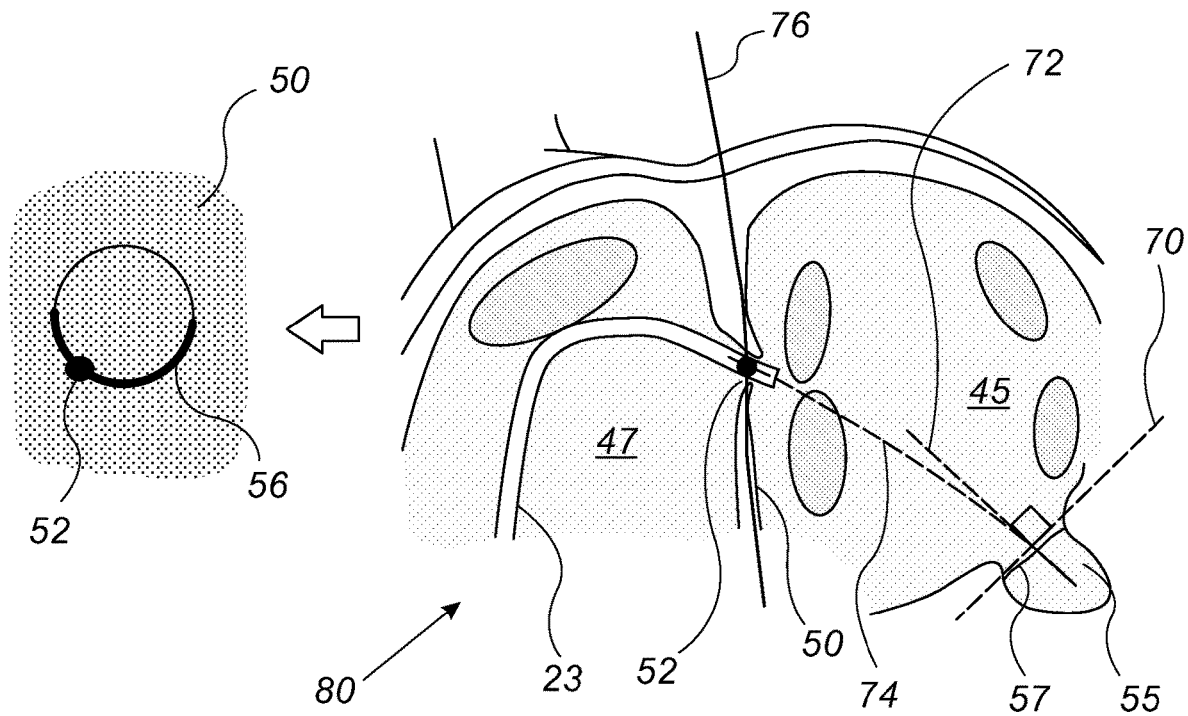
FIG. 2 is a schematic, pictorial illustration of a method of finding one or more candidate locations for septum penetration for the sheath of the catheter of FIG. 1, in accordance with an embodiment of the present invention.

FIG. 2 is a schematic, pictorial illustration of a method of finding one or more candidate locations for septum 50 penetration of sheath 23 of catheter 21 of FIG. 1, in accordance with an embodiment of the present invention. The right-hand side of the figure is a side cross-section of the heart, and the left-hand side is a frontal view of the septum. The aim of the technique is to enable best access of LAA 55 (shown in anatomical map 80) with catheter 21 carrying LAA occlusion device 40. A suitable way to achieve this is to advance the distal end of shaft 22 of catheter 21 at direction 66 (shown in FIG. 1) that is largely normal to ostium 57, at the defined surface of the ostium.

To this end, processor 41 uploads map 80 and defines a landing site for the LAA occlusion device as a plane 70 that the processor fits to ostium 57 of the LAA. As seen, plane 70 is substantially parallel to the LAA ostium at the landing site. Processor 41 then calculates a normal 72 to plane 70.

Using predefined mechanical properties of sheath 23 used for delivering LAA occlusion device 40, such as properties exemplified above, processor 41 calculates a plurality of curves 74 between normal 72 and plane 70 and septum 50. As noted above, each curve 74 (i) has one end that is tangent to the normal, (ii) has a second end touching the septum, and (iii) comply with specified mechanical properties of the sheath. This way the processor creates, at one or more respective intersections of curves 74 with, for example, a plane 76 the processor fits to septum 50, one or more respective potential access points for the transseptal puncture. The locations on septum 50 of the multiple potential access points are represented as a semicircular curve 56, where a particular selection is location 52 of FIG. 1 on semicircle 56.

As seen, processor 41 overlays the potential access points on anatomical map 80 presented to a physician performing the LAA occlusion procedure to, for example, assist in selecting a most suitable approach to the LAA with the catheter. In that sense, if no septum position is found to be good enough, the physician may try to model another sheath, or model a superior vena cava approach.

The example technique shown in FIG. 2 is chosen purely for the sake of conceptual clarity. In particular curve 56 has been simplified for clarity of presentation. Moreover, different access approaches to RA 47 generate entirely different multiple potential access points (e.g., different from curve 56).

Figure 3:
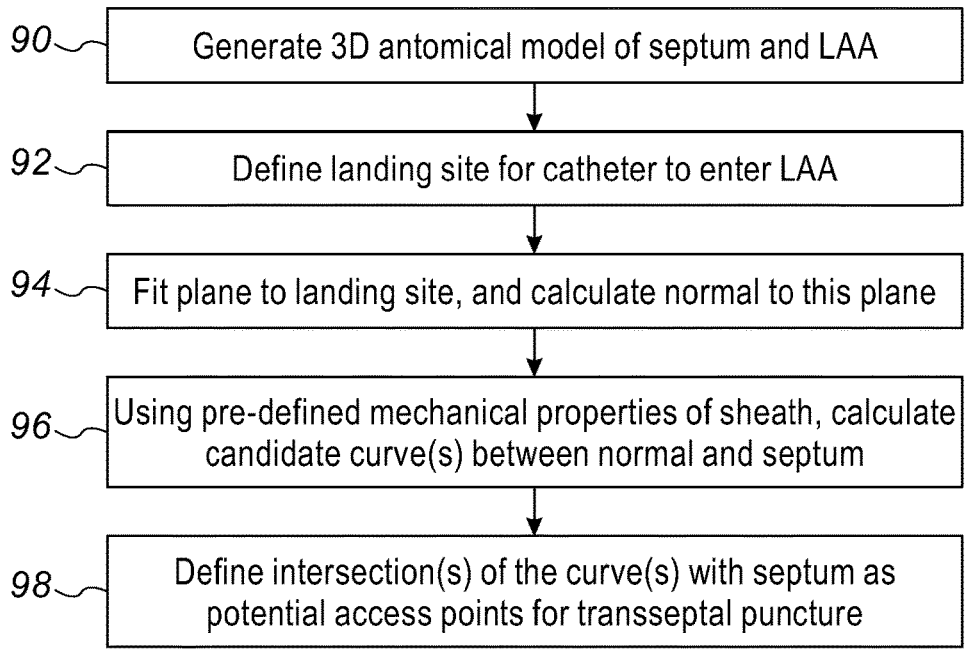
FIG. 3 is a flow chart that schematically describes a method of finding one or more candidate locations for septum penetration for a sheath of the catheter of FIG. 1, in accordance with an embodiment of the present invention.

FIG. 3 is a flow chart that schematically describes a method of finding one or more candidate locations 52 for septum penetration for a sheath of a catheter, in accordance with an embodiment of the present invention. The algorithm, according to the presented embodiment, carries out a process that begins with processor 41 generating (e.g., uploading from memory 35) an anatomical map 80 comprising septum 50 and LAA 55, at an anatomical map generation step 90.

Next, processor 41 defines a landing site for LAA occlusion device 40 by identifying ostium 57 of LAA 55, at a landing site definition step 92.

Next, the processor fits a plane 70 to ostium 57 and subsequently calculates normal 72 to plane 70, at a geometric construction step 94.

Using predefined mechanical properties of sheath 23 used to deliver LAA occlusion device 40, processor 41 calculates one or more candidate curves 74 between normal 72 of plane 70 and septum 50, at candidate curve derivation step 96.

Using curves 74, the processor calculates the multiple potential access points 56 on septum 50, as described above, at transseptal puncture locations calculation step 98.

The example flow chart shown in FIG. 3 is chosen purely for the sake of conceptual clarity. For example, additional steps, such as considering another access to RA 47 and subsequently repeating steps 94-98, are omitted from the purposely highly simplified flow chart.

Although the embodiments described herein mainly address the left atrium appendage, the technique described herein can also be used in other cardiac catheter applications of the LA, such as in electrophysiological mapping of the LA and pulmonary vein isolation. In particular, the disclosed technique may be applied to plan a landing site at an ostium a pulmonary vein (PV) for a catheter used in electrophysiological sensing and/or for ablation, such as a balloon catheter, a basket catheter, a lasso catheter, a multi-arm catheter, or a tip catheter.

Moreover, the disclosed technique may be applied with other LA treatment sites (e.g., Mitral valve) and for other catheter-carried devices (e.g., artificial valve).

It will thus be appreciated that the embodiments described above are cited by way of example, and that the present invention is not limited to what has been particularly shown and described herein above. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
   receiving ultrasound data from an invasive ultrasound probe inserted into a heart of a patient;
   using a processor, generating an anatomical map based at least in part on the ultrasound data, the anatomical map comprising a representation of at least part of the heart of the patient;
   identifying a septum and a Left Atrial Appendage (LAA) of the heart of the patient in the anatomical map;
   defining on the anatomical map an entry surface over which a medical device, which is to be delivered via a sheath that penetrates the septum, is to engage with the LAA;
   calculating a normal to the entry surface;
   calculating a plurality of curves that each (i) have one end that is tangent to the normal, (ii) have a second end touching the septum, and (iii) comply with specified mechanical properties of the sheath;
   deriving from the curves, multiple candidate locations on the septum for transseptal puncture with the sheath;
   presenting the multiple candidate locations to a user, the multiple candidate locations being represented as multiple candidate locations disposed along a semicircular curve; and wherein at least one of the multiple candidate locations is used by the user for puncturing the septum.

2. The method according to claim 1, wherein the specified mechanical properties of the sheath comprise a minimal radius of curvature of the sheath obtainable inside the heart by external manipulation of the sheath.

3. The method according to claim 1, wherein defining the entry surface comprises:
   delineating an ostium of the LAA on the anatomical map; and
   best fitting a plane to the delineated ostium.

4. The method according to claim 1, wherein calculating the curves depends on whether an access position of the sheath to a right atrium (RA) of the heart is from an inferior vena cava or from a superior vena cava.

5. The method according to claim 1, wherein the medical device is an LAA occlusion device.

6. The method according to claim 1, wherein the medical device is one of a balloon catheter and a basket catheter.

7. The method according to claim 1, wherein presenting the multiple candidate locations comprises presenting the sheath, the entry surface, the normal and the multiple candidate locations on the septum, using a three-dimensional (3D) mapping system.

8. A system, comprising:
   a processor; and
   a memory storing instructions thereon that, when executed by the processor, are configured to cause the system to:
   receive ultrasound data from an invasive ultrasound probe inserted into a heart of a patient, the ultrasound data comprising data indicative of at least part of the heart of the patient;
   generate an anatomical map based at least in part on the ultrasound data, the anatomical map comprising a representation of at least part of the heart;
   identify a septum and a Left Atrial Appendage (LAA) of the heart in the anatomical map;
   define on the anatomical map an entry surface over which a medical device, which is to be delivered via a sheath that penetrates the septum, is to engage with the LAA;
   calculate a normal to the entry surface;
   calculate a plurality of curves that each (i) have one end that is tangent to the normal, (ii) have a second end touching the septum, and (iii) comply with specified mechanical properties of the sheath;
   derive, from the curves, multiple candidate locations on the septum, for transseptal puncture with the sheath; and
   output, to a display, the multiple candidate locations for view by a user, the multiple candidate locations being represented as multiple candidate locations disposed along a semicircular curve, wherein at least one of the multiple candidate locations is used by the user for puncturing the septum.

9. The system according to claim 8, wherein the specified mechanical properties of the sheath comprise a minimal radius of curvature of the sheath obtainable inside the heart by external manipulation of the sheath.

10. The system according to claim 8, wherein the processor is configured to define the entry surface by:
    delineating an ostium of the LAA on the anatomical map; and
    best fitting a plane to the delineated ostium.

11. The system according to claim 8, wherein the processor is configured to calculate the curves depending on whether an access position of the sheath to a right atrium (RA) of the heart is from an inferior vena cava or from a superior vena cava.

12. The system according to claim 8, wherein the medical device is an LAA occlusion device.

13. The system according to claim 8, wherein the medical device is one of a balloon catheter and a basket catheter.

14. The system according to claim 8, wherein the processor is configured to present the multiple candidate locations by presenting the sheath, the entry surface, the normal and the multiple candidate locations on the septum, using a three-dimensional (3D) mapping system.

* * * * *